(12) United States Patent
Weiss et al.

(10) Patent No.: US 11,642,429 B2
(45) Date of Patent: *May 9, 2023

(54) ORAL DEVICE CONTAINER AND ORAL DEVICE SANITATION SYSTEM

(71) Applicant: Custom Club, Inc., Scottsdale, AZ (US)

(72) Inventors: Craig Weiss, Paradise Valley, AZ (US); Blair Feldman, Paradise Valley, AZ (US); Quinn Fitzgerald, San Francisco, CA (US); Chloe Georgiades, San Francisco, CA (US); Elliot Raderman, San Francisco, CA (US)

(73) Assignee: CUSTOM CLUB, INC., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/826,902

(22) Filed: May 27, 2022

(65) Prior Publication Data

US 2022/0288262 A1 Sep. 15, 2022

Related U.S. Application Data

(63) Continuation of application No. 17/406,173, filed on Aug. 19, 2021, now Pat. No. 11,344,644, which is a
(Continued)

(51) Int. Cl.
*A61L 2/26* (2006.01)
*F21V 8/00* (2006.01)
*A61L 2/10* (2006.01)

(52) U.S. Cl.
CPC .................... *A61L 2/26* (2013.01); *A61L 2/10* (2013.01); *G02B 6/0036* (2013.01);
(Continued)

(58) Field of Classification Search
CPC ........ A61L 2/26; A61L 2/10; A61L 2202/122; A61L 2202/121; A61L 2202/11; A61L 2202/24; G02B 6/0036
See application file for complete search history.

(56) References Cited

U.S. PATENT DOCUMENTS 3,518,988 A 7/1970 Gores
4,873,446 A * 10/1989 Kreitmair ............ A61C 19/003
250/455.11
(Continued)

FOREIGN PATENT DOCUMENTS

TW M307393 U 3/2007

OTHER PUBLICATIONS

International Search Report and Written Opinion dated Oct. 15, 2021 in International Patent Application No. PCT/US2021/021144 (14 pages, in English).

*Primary Examiner* — David A Vanore
(74) *Attorney, Agent, or Firm* — Bookoff McAndrews PLLC

(57) ABSTRACT

An oral sanitation system may include a case including: a support portion defining a lower end of the case; and a container portion extending from the support portion. The container portion may define a wall extending from the support portion to a top end of the container portion. The oral sanitation system may further include a closure including a lid formed with a peripherally-extending wall; a lower cavity defined by the wall of the container portion; an upper cavity defined by the peripherally-extending wall of the closure; and a light-guiding floor that is substantially transparent to UVC light, the light-guiding floor forming a bottom of the container portion that is surrounded by the wall.

19 Claims, 6 Drawing Sheets

Related U.S. Application Data continuation of application No. 17/192,690, filed on Mar. 4, 2021, now Pat. No. 11,110,192.

(60) Provisional application No. 62/986,276, filed on Mar. 6, 2020.

(52) U.S. Cl.
CPC ...... *A61L 2202/11* (2013.01); *A61L 2202/121* (2013.01); *A61L 2202/122* (2013.01); *A61L 2202/24* (2013.01)

(56) References Cited

U.S. PATENT DOCUMENTS

| | | | |
|---|---|---|---|
| 5,611,355 A | 3/1997 | Hilsen | |
| 5,899,691 A | 5/1999 | Parker et al. | |
| 6,415,794 B1 | 7/2002 | Kittelsen et al. | |
| 6,505,626 B2 | 1/2003 | Kittelsen et al. | |
| 6,505,627 B2 | 1/2003 | Kittelsen et al. | |
| 6,505,628 B2 | 1/2003 | Kittelsen et al. | |
| 6,508,251 B2 | 1/2003 | Kittelsen et al. | |
| 6,510,853 B1 | 1/2003 | Kittelsen et al. | |
| 6,539,943 B1 | 4/2003 | Kittelsen et al. | |
| 6,588,430 B2 | 7/2003 | Kittelsen et al. | |
| 6,598,605 B1 | 7/2003 | Kittelsen et al. | |
| 6,626,180 B1 | 9/2003 | Kittelsen et al. | |
| 6,675,806 B2 | 1/2004 | Kittelsen et al. | |
| 6,675,807 B2 | 1/2004 | Kittelsen et al. | |
| 6,691,710 B2 | 2/2004 | Kittelsen et al. | |
| 7,156,774 B2 | 1/2007 | Mohindra | |
| 7,549,423 B1 | 6/2009 | Hirshberg | |
| 7,637,262 B2 | 12/2009 | Bailey | |
| 7,888,656 B2* | 2/2011 | Freedgood | A61L 2/10 250/455.11 |
| D639,439 S | 6/2011 | Raad | |
| 8,074,658 B2 | 12/2011 | Kittelsen et al. | |
| 8,113,206 B2 | 2/2012 | Roettger et al. | |
| 8,156,940 B2 | 4/2012 | Lee | |
| 8,166,976 B2 | 5/2012 | Webster et al. | |
| 8,567,408 B2 | 10/2013 | Roettger et al. | |
| 8,585,401 B2 | 11/2013 | Moses | |
| 9,545,332 B2 | 1/2017 | Luco | |
| 9,655,695 B2 | 5/2017 | Ross | |
| 9,668,827 B2 | 6/2017 | Roettger et al. | |
| 9,820,882 B2 | 11/2017 | Liptak et al. | |
| 9,844,424 B2 | 12/2017 | Wu et al. | |
| 9,861,513 B2 | 1/2018 | Rayek et al. | |
| 9,943,386 B2 | 4/2018 | Webber et al. | |
| 9,943,991 B2 | 4/2018 | Tanugula et al. | |
| 9,949,868 B2 | 4/2018 | Kim et al. | |
| 11,110,192 B1* | 9/2021 | Weiss | A61C 19/02 |
| 2003/0034459 A1* | 2/2003 | Bonin | A61L 2/06 250/491.1 |
| 2004/0118427 A1 | 6/2004 | Palfy et al. | |
| 2005/0220665 A1* | 10/2005 | Ding | A61B 1/123 422/128 |
| 2006/0242788 A1* | 11/2006 | Day | A61L 2/10 15/363 |
| 2007/0197876 A1 | 8/2007 | Lane | |
| 2009/0256085 A1* | 10/2009 | Thiruppathi | A61L 2/10 250/492.1 |
| 2009/0311149 A1* | 12/2009 | Freedgood | A61L 2/10 422/186.3 |
| 2010/0275930 A1 | 11/2010 | Evans | |
| 2010/0326484 A1* | 12/2010 | Wu | A61L 2/24 134/140 |
| 2013/0118507 A1 | 5/2013 | Chappuis | |
| 2014/0000633 A1 | 1/2014 | Hernandez | |
| 2014/0069441 A1 | 3/2014 | Moses | |
| 2015/0075540 A1 | 3/2015 | Dye | |
| 2015/0272773 A1 | 10/2015 | Rico et al. | |
| 2015/0305919 A1 | 10/2015 | Stubbs et al. | |
| 2016/0120619 A1 | 5/2016 | Bons | |
| 2017/0000643 A1 | 1/2017 | Gelb et al. | |
| 2017/0014262 A1 | 1/2017 | Dietz | |
| 2017/0020716 A1 | 1/2017 | Hart et al. | |
| 2017/0120135 A1 | 5/2017 | Engel et al. | |
| 2017/0202644 A1 | 7/2017 | Ross | |
| 2017/0282451 A1 | 10/2017 | Layzell et al. | |
| 2018/0000564 A1 | 1/2018 | Cam et al. | |
| 2018/0014380 A1 | 1/2018 | Komicki et al. | |
| 2018/0071135 A1 | 3/2018 | Ingemarsson-Matzen | |
| 2018/0093001 A1* | 4/2018 | Georgeson | A61L 2/0047 |
| 2018/0117191 A1* | 5/2018 | Shell | B65B 55/02 |
| 2018/0133581 A1 | 5/2018 | Segal | |
| 2018/0193182 A1 | 7/2018 | Wiffen | |
| 2018/0193183 A1 | 7/2018 | Kim et al. | |
| 2018/0207020 A1 | 7/2018 | Hart et al. | |
| 2019/0021901 A1 | 1/2019 | LeBlanc et al. | |
| 2019/0344150 A1 | 11/2019 | Dreve | |

\* cited by examiner

– 1 –
ORAL DEVICE CONTAINER AND ORAL DEVICE SANITATION SYSTEM

CROSS-REFERENCE TO RELATED APPLICATIONS

This patent application is a continuation of and claims the benefit of priority to U.S. patent application Ser. No. 17/406,173, filed on Aug. 19, 2021, which is a continuation of and claims the benefit of priority to U.S. patent application Ser. No. 17/192,690, filed on Mar. 4, 2021, which claims benefit of priority to U.S. Provisional Application No. 62/986,276, filed on Mar. 6, 2020, the entireties of each of which are incorporated herein by reference.

TECHNICAL FIELD

The present disclosure relates generally to a container for an oral device such as a mouthguard, retainer, clear aligners, or other dental, medical, or personal devices associated with use in the mouth, and a sanitation system useful with such oral devices.

BACKGROUND

Oral devices, such as mouthguards, are used by individuals to protect at least their teeth, upper jaw (maxilla), and/or lower jaw (mandible) from injury during athletic events. Cases or containers for mouthguards are used to store and protect the mouthguard when not in use. Similar dental devices, such as retainers, night guards or other bruxism-care devices, aligners, etc., can be stored in cases to reduce the likelihood that these devices are misplaced or damaged. However, these cases are themselves easily misplaced, frequently become dirty, and are difficult to clean or otherwise inconvenient and unsanitary. Microbes and viruses present on the dental device may be transferred to the case, whereupon the microbes may remain present and active. In some cases, these microbes may potentially increase in number, and can be re-introduced into a user's mouth. Conventional cases are typically used to store a retainer, night guard, or related device that is retrieved for wear overnight. However, the case may be especially difficult to identify and locate in a dark environment such as a bedroom or bathroom. There is a need, therefore, for a more easily identifiable, secure, and sanitary oral device container.

The oral device container and sanitizing system of the present disclosure may solve one or more of the problems set forth above and/or other problems in the art. The scope of the current disclosure, however, is defined by the attached claims, and not by the ability to solve any specific problem.

SUMMARY

In one aspect of the present disclosure, an oral sanitation system may include a case including: a support portion defining a lower end of the case; and a container portion extending from the support portion. The container portion may define a wall extending from the support portion to a top end of the container portion. The oral sanitation system may further include a closure including a lid formed with a peripherally-extending wall; a lower cavity defined by the wall of the container portion; an upper cavity defined by the peripherally-extending wall of the closure; and a light-guiding floor that is substantially transparent to UVC light, the light-guiding floor forming a bottom of the container portion that is surrounded by the wall.

In a further aspect of the present disclosure, an oral sanitation system may comprise a disinfecting base; a source of UVC light disposed within the disinfecting base; a container portion defining a wall extending to a top end of the container portion, the container portion including an opening configured for ventilation; a closure including an opaque lid that is positionable over the disinfecting base so as to cover an oral device supported by the container portion; a lower cavity defined by the wall of the container portion; and an upper cavity defined within the opaque lid, wherein the opaque lid is sized so as to permit leakage of at least some of the UVC light outside of the disinfecting base, and the closure when the opaque lid covers the oral device supported by the container portion.

In a further aspect according to the present disclosure, a method for an oral sanitation device, may include: forming a case including: a support portion at a lower end of the case; a container portion extending from the support portion, the container portion having a wall defining a lower cavity sized to receive an oral device for sanitation; and a light-guiding floor at a bottom of the lower cavity configured to support the oral device; forming a lid having a peripherally-extending wall defining an upper cavity, the lid shaped so as to at least partially enclose the lower cavity; and defining a path for light to travel toward the lower cavity through the light-guiding floor such that a visible amount of light exits from the base and the lid.

DETAILED DESCRIPTION

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus.

Relative terms, such as, "substantially" and "generally," are used to indicate a possible variation of ±10% of a stated or understood value.

Figure 1:
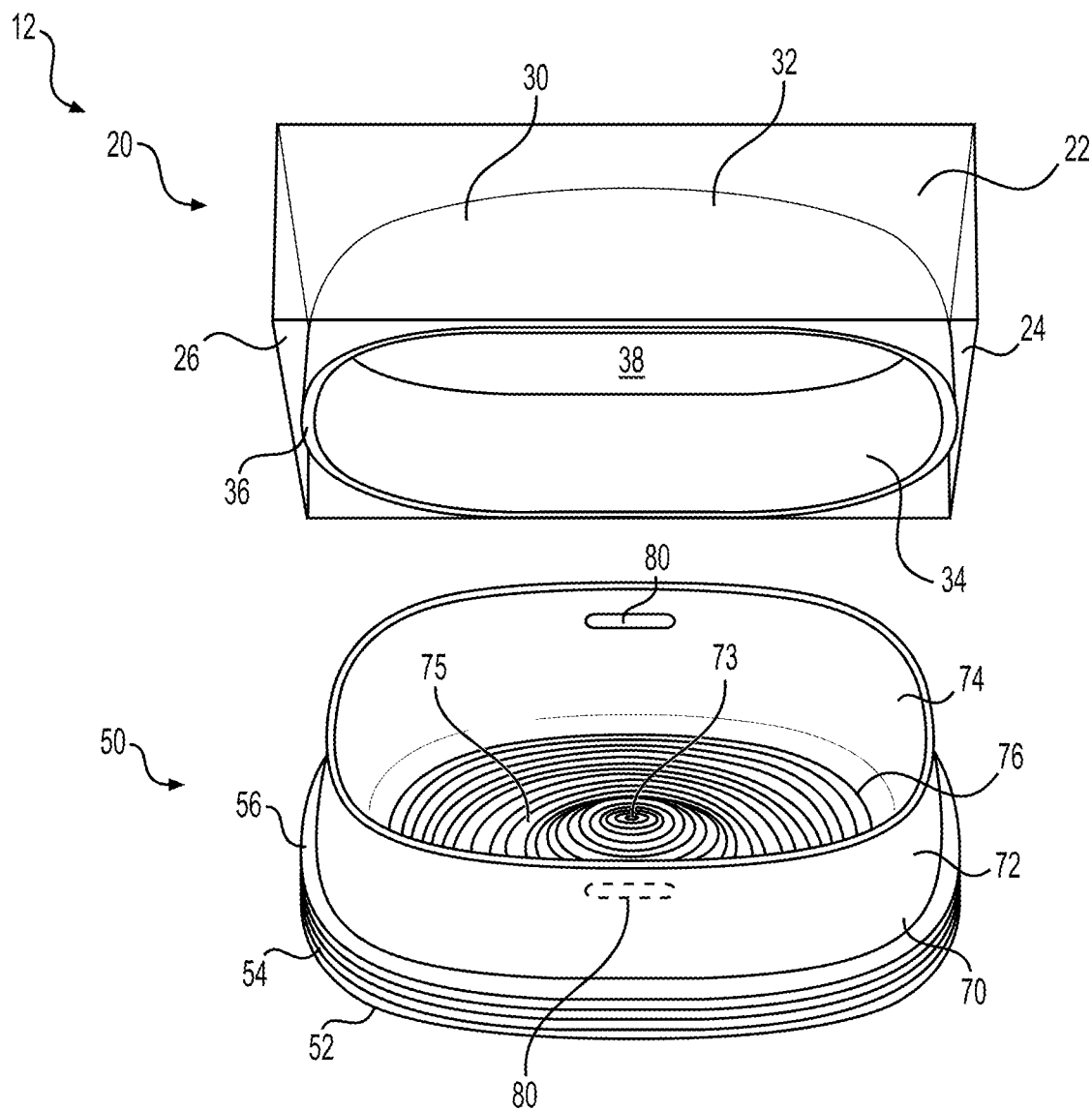
FIG. 1 shows a front perspective view of an oral device container of an oral disinfection system according to an embodiment of the disclosure.

FIG. 1 shows a front perspective view of an oral disinfection system 12 according to an embodiment of the disclosure. Oral disinfection system 12 may include a plurality of separate pieces for storing and disinfecting an oral appliance or dental device such as a retainer, bruxism-care device, aligner, etc. (e.g., oral device 14 as shown in FIG. 3A). As shown in FIG. 1, oral disinfection system 12 may include a two-piece assembly including a closure 20 and case 50. System 12 may have an overall height ranging from about 25 mm to about 50 mm, a depth ranging from about 73 mm to about 85 mm, and a width ranging from about 73 mm to about 85 mm. Closure 20 may have an overall height ranging from about 19 mm to about 21 mm.

Closure 20 may include a lid 30 that forms a cap or cover that may be placed on case 50. A peripherally-extending wall 32 of lid 30 may extend from an upper cap 38 to define an upper cavity 34. Wall 32 and upper cavity 34 may have any suitable shape, and may define, for example, a circle, ovoid, rectangle, square, as well as other polygonal or irregular shapes. A surface of wall 32 may form a rim 36 that defines a bottom lip of lid 30. While closure 20 and case 50 are illustrated as separate components, closure 20 may instead be permanently or removably affixed to case 50, e.g., by one or more hinges. In addition, closure 20 may be securely and durably fit to case 50, to provide closure for ease of storage and carrying of the system 12 for travel.

Closure 20 may also include an illuminable body, such as a body 22, which may extend outward from a peripheral surface of lid 30. In some embodiments, closure 20 may have a rectangular exterior surface formed by walls 24, and a rounded interior surface shaped to match a shape of an exterior shape of lid 30. Each wall 24 of body 22 may itself form a planar rectangular side surface, thereby collectively forming a prism as the exterior shape of the closure 20. Body 22 may be formed of a relatively hard, clear or translucent material, such as an engineered material, such as acrylic or plastic, and, more specifically, Tritan™, Lucite, thermoplastic elastomer (TPE) (such as Food Contact Safe TPE), or food-safe silicone. For example, body 22 may be formed of a hard plastic within which lid 30, which may be opaque, is embedded (e.g., by molding). In addition, lid 30 may be formed of a relatively hard, clear, or translucent material, such as an engineered material, such as acrylic or plastic, and, more specifically, such as Tritan™, Lucite, polycarbonate (PC), thermoplastic elastomer (TPE) (such as Food Contact Safe thermoplastic elastomer (TPE)), or food-safe silicone. In addition or alternatively, components of closure 20 may be formed from a biocompatible material. Further, closure 20 may be shatterproof and may be configured to remain intact and secure to case 50 even when dropped from a height of several feet, for example, up to 3 feet. When provided as a translucent illuminable body or prism, body 22 may include coloring and may be colored differently than lid 30, case 50, or both. Alternatively, illuminable body 22 may be a translucent, colored body that has the same color or a similar color as one or both of lid 30 and case 50. As one particular example, the body 22 may be crystal clear in color, formed of clear Tritan™, with a 90% gloss finish, while the lid 30 may be PMS 11-4800 TPX in color, formed of silicone (80 Shore A), with MT-11004 finish, and the body 22 and the lid 30 may be insert molded together. As another example, the entirety of the closure 20 may be PMS 11-4800 TPX in color, formed of silicone (85 Shore A), with MT-11004 finish, and may include a high-gloss, debossed logo (e.g., personalization, as described below). The above-described shape and materials of body 22 may be configured to distribute light to an exterior thereof to become illuminated in a substantially regular manner. For this reason, a surface finish and a clarity of at least a portion of closure 20 may be selected so as to provide ambient light, as described below. A bottom face 26 of body 22 may be aligned or flush with rim 36. Alternatively, bottom face 26 may extend below rim 36, or terminate at a height between rim 36 and cap 38.

Case 50 may form a structure configured to receive a dental device and may further be configured to sanitize or disinfect a dental device stored therein. In an exemplary configuration, case 50 may include a lower support portion 52 from which an upper container portion 70 extends. Support portion 52 may include a peripherally-extending outer surface 54. As shown in FIG. 1, surface 54 may be formed by a textured surface having a plurality of grooves and recesses. An upward-facing surface of support portion 52 may form a support surface 56. Support surface 56 may have substantially the same shape as rim 36 and may be configured to receive rim 36 so as to support both body 22 and lid 30 of closure 20. Case 50 may also include a bottom insert, to which a personalization 62, described below, may be added. The components of case 50, including support portion 52 and container portion 70, may be formed of a suitable material, such as an engineered material, such as plastic or silicone. More specifically, the material may be Tritan™, Lucite, polycarbonate (PC), TPE (such as Food Contact Safe TPE), or food-safe silicone, such as 80 Shore A silicone. A color of the components of case 50 may be, for example, PMS 11-4800 TPX, translucent white, neutral clear, PMS Grey B, or translucent with a light-diffusing additive. A finish of the components of case 50 may be MT-11004, 15% gloss, 90% gloss, or soft touch. As a more specific example, body 22 may be formed of polycarbonate, in color PMS 11-4800 TPX, with a finish of MT-11004, container portion 70 may be formed of silicone, 80-Shore A, in color PMS 11-4800 TPX, with a finish of MT-11004, and lid 30 may be formed of polycarbonate, in color translucent white, with a finish of 15% gloss. The materials, colors, and finishes of the components of case 50 are not, however, limited to those described above.

In some aspects, case 50 may be formed such that connection points between the components thereof are not visible. In addition, case 50 may be configured to remain intact when dropped from a height of several feet, for example, 3 feet. In some instances, system 12, including case 50 and closure 20, may be rated as IP67 (ingress protection rating set by the International Electrotechnical Commission).

Container portion 70 may include an upwardly-extending peripheral wall 72 that defines an internal lower cavity 74. A bottom of lower cavity 74 may be defined by a textured light-guiding floor 76. Light-guiding floor 76 may have a raised center portion or central protrusion 73, surrounded by a generally-circular recess 75, so as to form a macro-texture of light-guiding floor 76. The generally-circular recess 75 may be shaped, for example, to receive opposite arches of dental device 14 (FIG. 3A). An outer periphery of light-guiding floor 76 may be raised above recess 75.

One or more sides of peripheral wall 72 may have an opening 80 forming an air vent for permitting ventilation of case 50. While two symmetrically arranged openings 80 are shown in FIG. 1, one, three, four, or more symmetrically or asymmetrically arranged openings 80 may be present along (e.g., extending through) wall 72. Each of the openings 80 may extend approximately 5 mm to approximately 6 mm in length, and about 1 mm to about 2 mm in height along a peripheral direction of wall 72.

Support portion 52 and container portion 70 of case 50 may be formed together as a single monolithic structure, or may instead be separate pieces that are permanently joined together. Support portion 52 may be formed of any suitable material, including polymer materials having antimicrobial properties and/or antimicrobial coatings. The same or similar materials may be included in container portion 70. If desired, textured surface 54 may be formed of a compliant material.

Figure 2:
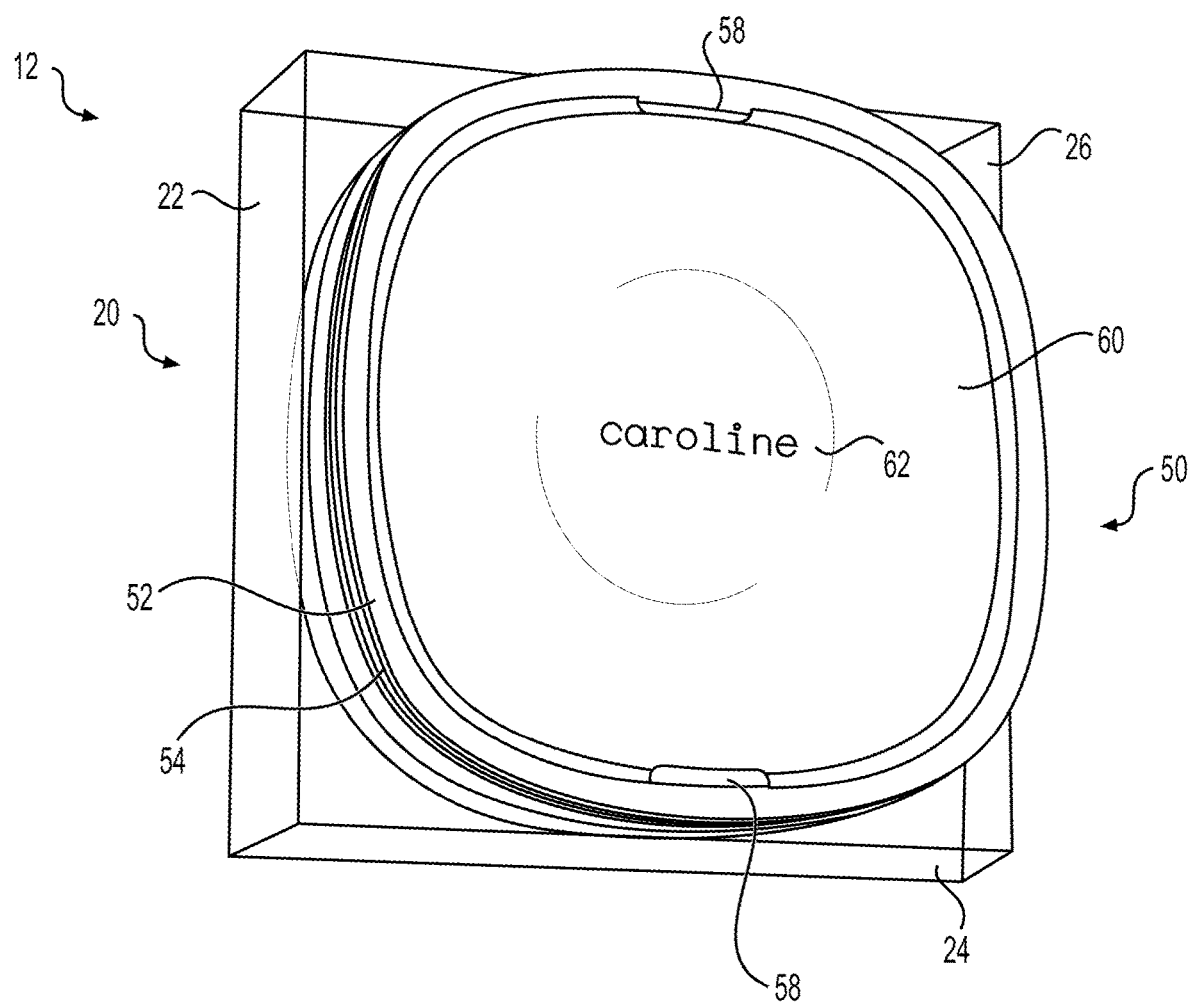
FIG. 2 shows a bottom perspective view of the oral device container shown in FIG. 1.

FIG. 2 is a bottom perspective view showing closure 20 and case 50 of oral disinfection system 12 in an assembled state. In this assembled or closed position, closure 20 may surround and close lower cavity 74. A bottom surface 60 may define the bottom of case 50 so as to support case 50 and closure 20. One or more vents 58 formed at the periphery of bottom surface 60 may extend to an interior of case 50, e.g., so as to extend through light-guiding floor 76, such that upper and lower cavities 34 and 74 fluidly communicate with an exterior of case 50. If desired, a region of support portion 52, such as bottom surface 60, may include a personalization 62, such as a relief, which may contain name, address, contact, or any other desired information or ornamental decoration. In addition or alternatively, the personalization 62 may be provided on closure 20. Personalization 62 may be added in any suitable manner, such as by laser etching a portion of case 50, closure 20, or both.

Illuminable body 22 of closure 20 may include portions that extend outward with respect to case 50 when closure 20 and case 50 are assembled. For example, as shown in FIG. 2, a plurality of (e.g., four) portions may define a body 22 that extends outward with respect to case 50. These portions may have an approximately triangular cross-sectional shape (e.g., with a curved surface and two straight edges, as shown in FIG. 2). Each of these outwardly-extending portions may include a bottom face 26, for example. While each bottom face 26 may be formed as separately sections, bottom faces 26 may instead form a continuous surface at the bottom of body 22 and, if desired, the bottom of closure 20.

Figure 3B:
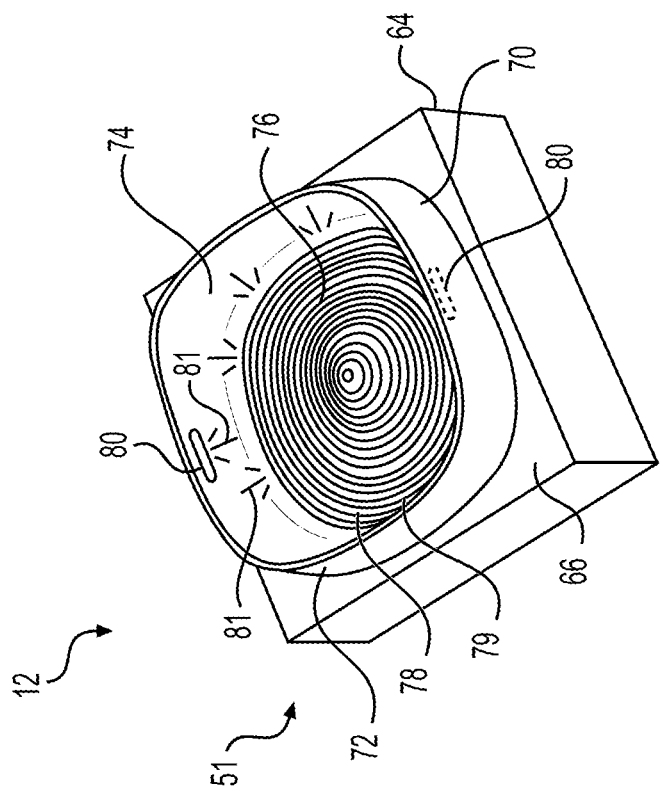
FIG. 3B is a view of the disinfecting base of FIG. 3A with the dental device removed and the disinfecting base activated.
Figure 3A:
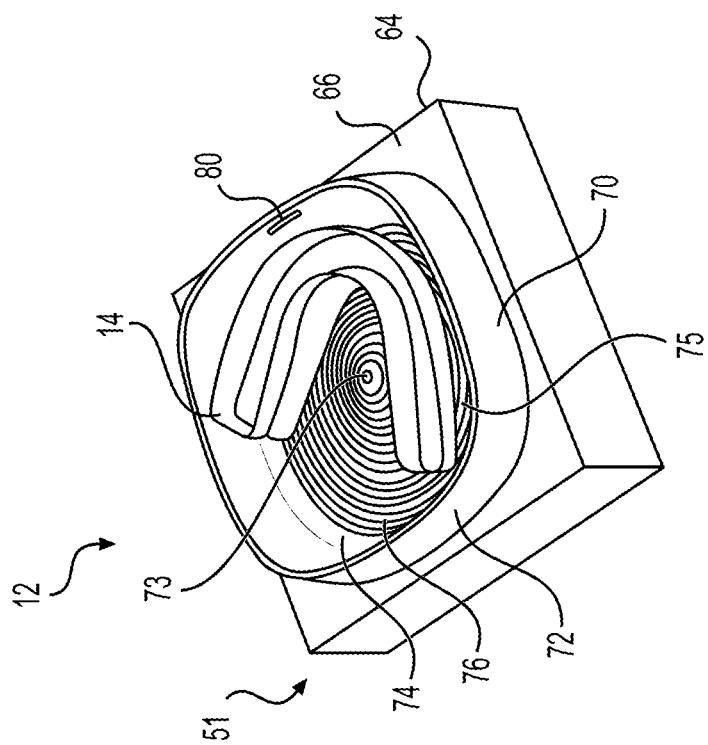
FIG. 3A is a view of a disinfecting base of the oral disinfection system containing a dental device according to an embodiment of the disclosure.

FIGS. 3A and 3B illustrate an exemplary disinfecting base 51 according to embodiments of the disclosure. Base 51 may be configured for use with closure 20 described above, for example, and may include a container portion 70 for receiving closure 20. In at least some aspects, base 51 may include a cavity (FIG. 4A) within which case 50, including support portion 52, may be received, such that container portion 70 of case 50 protrudes from base 51. For example, base 51 may include a substantially rectangular receiver portion 64 defining an upward-facing support surface 66 from which container portion 70 protrudes. In some aspects, receiver portion 64 may have a shape that is approximately the same as the shape of body 22 such that receiver portion 64 is configured to oppose, and if desired, contact and support, bottom face 26 (FIG. 2). Removably securing container portion 70 to receiver portion 64 may be desirable, for example, to facilitate cleaning or replacement of container portion 70, and/or of a light source secured within receiver portion 64. While container portion 70 may be removably secured to receiver portion 64 of disinfecting base 51, in some aspects, container portion 70 may instead be integrally-formed with receiver portion 64, allowing disinfecting base 51 to itself form a case.

Textured light-guiding floor 76 may be configured to support a dental device 14 contained within the lower cavity 74 defined by wall 72. Dental device 14, which may be a retainer, mouthguard, night guard, aligner, or other similar device, may be supported such that at least a portion of device 14 is received by recess 75 and positioned adjacent to one or more raised portions (e.g., central protrusion 73), as shown in FIG. 3A.

An interior of receiver portion 64 may include a suitable source of energy for generating radiation that inhibits or prevents microbial growth. For example, an interior of receiver portion 64 may secure a source of ultraviolet light. This ultraviolet light may be, for example, ultraviolet C ("UVC") light. By virtue of the UVC light, the dental device 14 may be sanitized when placed within the system 12, and exposed to the UVC light. That is, an intensity of the UVC light is suitable for sanitizing an object, such as the dental device 14, placed within the system 12, while meeting regulatory certifications for safety and emissions relating to UVC light. For example, the UVC light may kill 90% to 100% of pathogens, for example, 99.9%, within a given amount of time when the dental device 14 is exposed to the UVC light. In one example, 99% of pathogens may be killed within 60 minutes of exposure of the dental device 14 to the UVC light. In addition, by virtue of the UVC light, the system 12 may promote safety in use of the dental device 14, particularly with respect to oral hygiene.

As shown in FIG. 3B, when a source of UVC light (e.g., light source 82, FIG. 4A) is activated, light 81 may pass through light-guiding floor 76, formed of a substantially UVC-transparent material, so as to fill lower cavity 74. Light 81 may include UVC light having a wavelength within a range of about 100 nm and about 280 nm. For example, light 81 may include UVC light having a wavelength (e.g., a peak emission) within about 100 nm and about 280 nm. In particular, light 81 may include light emitted with a peak emission of about 220 nm and about 270 nm, or about 250 nm to about 260 nm. As described below, light 81 may also include light having a wavelength within a spectrum of light visible to a user (e.g., violet light, blue light, etc.). Visible light may be used, for example, to provide a status light (indicating, for example, a charge state of system 12), or ambient light (such as when system 12 operates in a nightlight mode), while UVC light is used for sanitization and disinfection. Light source 82 may include a printed circuit board assembly (PCBA).

Light pipes or guides 80 may be formed so as to extend within wall 72 of container portion 70. In some aspects, light guides 80 may extend from light source 82 to the inner surface of wall 72 so as to facilitate cleaning of a dental device 14 with UVC light 81. Light 81 may be directed from an end face of light guides 80 that faces lower cavity 74, as described above. Light guides 80 may be formed of a suitable light-guiding material, such as a substantially UVC-transparent copolyester, such as Tritan. Alternatively, light guide 80 may include acrylic, polycarbonate, UVC-transparent glass, or other suitable materials. In some aspects, one or more light guides 80 may include an outwardly-facing end that directs light toward a space between walls 32 and 72 so as to facilitate leakage of a controlled amount of light outside of cavities 34 and 74, as described below.

In addition to light guides 80, the structure of light-guiding floor 76 may facilitate distribution of UVC light to a dental device supported thereon. For example, by providing a macro-textured recess 75, raised portions of floor 76 may surround portions of dental device 14. For example, a raised outer periphery of floor 76, as well as central protrusion 73 may direct at least some UVC light in a lateral direction toward a portion of device 14 resting in recess 75, thereby facilitating coverage of device 14 with UVC-containing light.

In order to facilitate drainage of moisture (e.g., moisture transferred from dental device 14), light-guiding floor 76 may include a micro-texture. In the exemplary configuration best shown in FIG. 3B, a plurality of ridges 78 and depressions 79 may be formed in floor 76. Depressions 79 may form fluid-receiving channels that draw away moisture from dental device 14. Additionally, ridges 78 and depressions 79 may tend to scatter light within lower cavity 74, promoting coverage of dental device 14 with UVC light for disinfection.

Figure 4A:
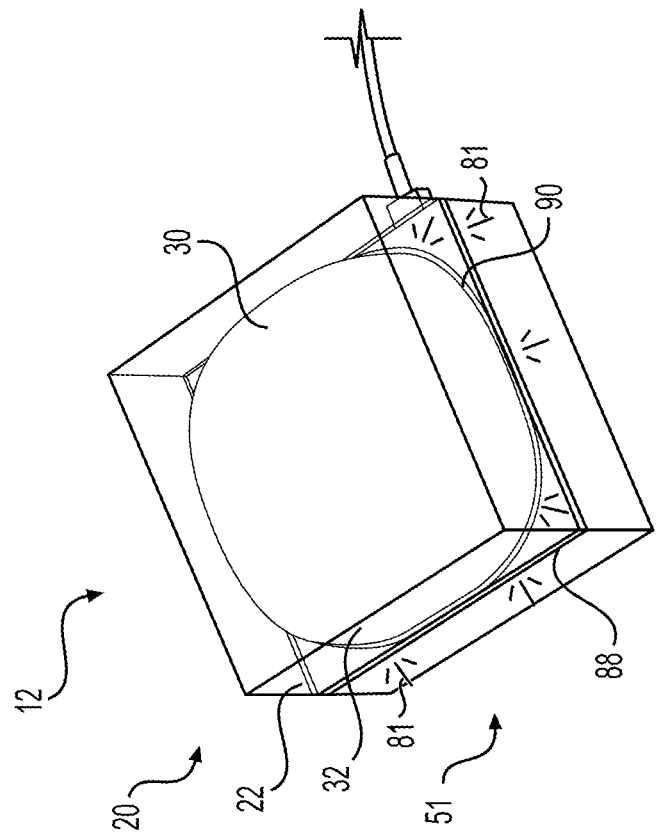
FIG. 4A is a view of the disinfecting base and closure of the oral disinfection system in an open position.

FIG. 4A is a view showing an exemplary configuration of disinfecting base 51 and closure 20 of system 12, with closure 20 in an open position and container portion 70 removed from receiver portion 64. Disinfecting base 51 may include a light source 82 secured within receiver portion 64. Light source 82 may be any suitable source configured to generate light 81. For example, light source 82 may include one or more UVC lamps (e.g., mercury lamps), UVC-emitting diodes or UVC LEDs, or xenon lamps. Light source 82 may be configured to generate the above-described light 81, including UVC light, which may also contain at least some light having a wavelength within the visible spectrum, in addition to germicidal UVC light. In some aspects, light source 82 may include a plurality of light-generating devices, including at least one light-generating device configured to generate UVC light, and at least one light-generating device configured to generate visible light (e.g., violet light, blue light, red light, green light, etc., that is visible to the human eye). Light source 82 may include a permanently-installed light-generating device(s) (e.g., a fixed LED module), or one or more replaceable light-generating devices (e.g., one or more replaceable bulbs). Light source 82 may be secured so as to direct light in a primarily upward direction, e.g., in a direction toward the interior of container portion 70, including lower cavity 74 (FIG. 3B). For example, the light source 82 may include one or more light-generating devices having an element directed toward container portion 70. Additionally or alternatively, light source 82 may include one or more reflectors, such as a reflective material and/or coating. Such coatings may be useful for increasing an amount of light directed toward container portion 70.

Oral disinfection system 12 may include a light source 82 configured to receive power supplied by a cable 86 via a connector 84. In the exemplary configuration illustrated in FIGS. 4A and 4B, connector 84 may be received by receiver portion 64. Receiver portion 64 may include a suitable receptacle (e.g., a universal serial bus (USB) receptacle) configured to receive connector 84 (e.g., a USB Type-C (USB-C) connector). Accordingly, connector 84 may be removable from receiver portion 64, to facilitate portability of disinfection system 12. Alternatively, light source 82 may receive power supplied by one or more batteries (not shown). The one or more batteries may be rechargeable via the connector 84 and the cable 86. A life of a battery may be, for example, up to two weeks of normal (e.g., daily, nightly, etc.) usage, or up to a dozen of more, e.g., 14, sanitization cycles (or other suitable predetermined timings). The one or more batteries may be rechargeable, and one or more indicators may be provided to indicate whether system 12 is charging, fully charged, and/or requires charging.

While light 81 is shown in FIG. 4A while closure 20 is separated from base 51 for purposes of illustration, in at least some aspects, it may be desirable to prevent UV light source 82 from generating light 81 when system 12 is in an open position, such as when closure 20 is separated (or pivoted) from base 51. System 12 may include a mechanism configured to disable light source 82 to prevent the generation of UV light when system 12 is in an open configuration. For example, an electronic switch, such as push-button switch (e.g., a microswitch), or another actuatable device may be secured within support surface 66 and configured to receive a protrusion extending from closure 20. Such a microswitch may, when activated, permit or enable generation of UV light by light source 82, while disabling light source 82 when closure 20 is separated from base 51 so as to disengage the microswitch. In addition or alternatively, light source 82 may be activated by pushing or pressing closure 20 onto base 51. In addition or alternatively, light source 82 may be automatically shut off when closure 20 is removed from base 51.

The location and arrangement of light source 82 is not limited to that shown in FIG. 4A. For example, light source 82 may be arranged as a downward-facing light. Alternatively or additionally, light source 82, may be arranged as a "light bar" on upward-facing support surface 66 of base 51, to project light substantially upwards from base 51, or a side-facing surface of base 51. In some aspects, light source 82 may be arranged on upward-facing support surface 66 in a rounded square, or a "squircle," configuration, following a shape of rim 36 and inner periphery of body 22 of closure 20. In some aspects, light source 82 may be arranged on upward-facing support surface 66 in a perimeter configuration, following a perimeter of upward-facing support surface 66. In addition, light source 82 may be arranged on an entirety of upward-facing support surface 66, as a planar light source. Further, light source 82 may include a plurality of light-emitting diodes (LEDs) arranged at or near the four corners of upward-facing support surface 66, in a path around a perimeter of upward-facing support surface 66, or distributed across upward-facing support surface 66. Still further, light source 82 may be arranged to emit light from the entirety of base 51 or a majority of base 51. Light source 82 may also be arranged so as to diffuse light toward a relief, such as a logo, provided in closure 20.

Figure 4B:
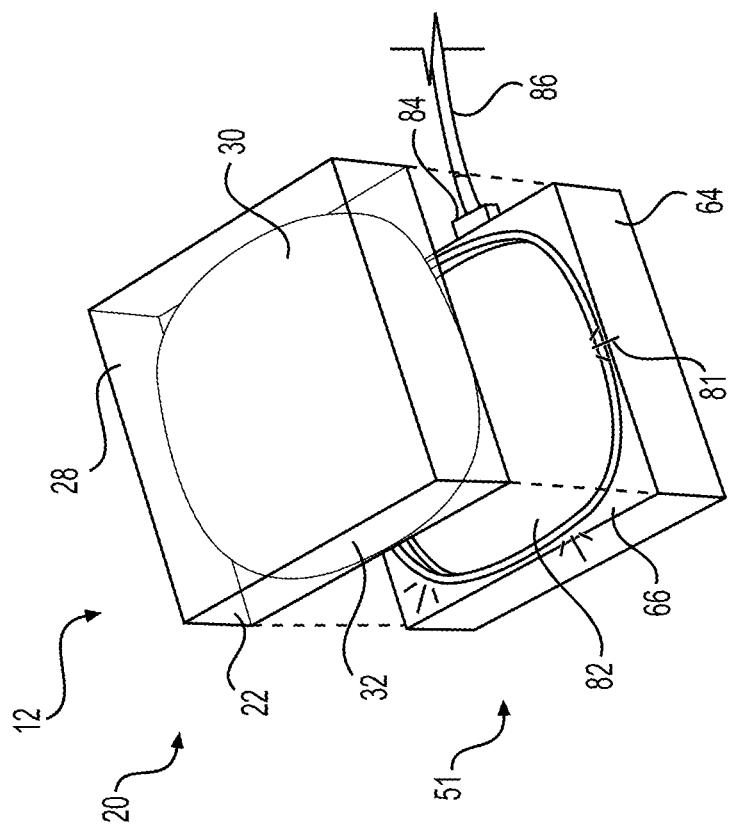
FIG. 4B is a view of the disinfecting base and closure of FIG. 4A in a closed position.

When light source 82 is activated and closure 20 is secured such that system 12 is in a closed position, UVC light may substantially fill the space formed by upper cavity 34 and lower cavity 74. This light may enter cavities 34 and 74 via light-guiding floor 76. As shown in FIG. 4B, at least some light 81 may leak from the enclosed cavities 34 and 74 so as to illuminate body 22. In this manner, the light 81 may provide a backlighting effect for the closure 20. For example, a controlled space or gap between an inner surface of wall 32 and an outer surface of wall 72 (see FIG. 1) may facilitate leaking of a controlled amount of light 81, including some visible light through closure 20. This light 81, which may have a blue appearance, may be indicative of a state of system 12. In particular, the presence of light 81 (e.g., blue light) may indicate that system 12 is actively disinfecting the interior of system 12, and a dental device 14 contained therein, via UVC light. If desired, system 12 may include circuitry (e.g., a timer, microprocessor, etc.) configured to deactivate light source 82, and thereby stop the application of UVC light, after a predetermined timing necessary to disinfect dental device 14. As an example, the predetermined timing, also referred to as a cycle, necessary to disinfect dental device 14 may be 60 minutes. The predetermined timing is not, however, limited to 60 minutes, and may be set to a greater or a lesser amount of time, or may be adjustable. The predetermined timing may be measured using a timer. The predetermined timing may also be set based on standards set forth by the National Science Foundation (NSF). In some aspects, after this predetermined timing, a different light source (e.g., a green light source) may be activated to indicate that disinfection is complete. Alternatively, the absence of light, or a different pattern (e.g., blinking or steady light) may indicate that disinfection is complete.

Additionally, system 12 may be configured for use in a continuous light mode or a nightlight mode in which illumination is provided indefinitely or for a desired period of time. For example, immediately following complete disinfection, or a predetermined time after disinfection, light 81 may be generated to present a desired color (or a white color), without the generation of UVC light. However, if desired, UVC light may be generated, in addition to visible light, during a continuous light or nightlight mode. In some aspects, system 12 may include circuitry for automatically transitioning to a continuous light or nightlight mode following complete disinfection. For example, system 12 may generate green light for a predetermined time to indicate disinfection is complete, and transition to a second color upon entering a nightlight mode. Still further, system 12 may operate in nightlight mode, for example, when motion-activated. In such an embodiment, system 12 may be equipped with a motion sensor.

Activation, deactivation, and durations of the lighting effects, namely, the visible light in the nightlight mode or in the continuous light mode, and/or the UVC light, may be programmable by the user and/or preset. In a case in which activation, deactivation, or durations of the lighting effects are programmable by the user, the user may set and/or program the timings for activation or deactivation, and/or durations via the circuitry provided in the system 12. The user may set and/or program the timings for activation or deactivation, and/or the durations by connecting a device, such as a smartphone or computer, to the system 12 via the connector 84 and the cable 86, with the device including software, such as an application (e.g., a smartphone app) for generating instructions to set and/or program the durations. In addition or alternatively, the system 12 may include a wireless transmitter and receiver for wirelessly communicating with a wireless-communication-enabled device of the user, such as a smartphone. For example, the wireless transmitter and receiver may be a Bluetooth transmitter and receiver configured to receive the instructions for setting and/or changing a timing of activation or deactivation, and/or a duration of a lighting effect from the device of the user.

Alternatively, activation, deactivation, and durations of the lighting effects may be controlled via one or more microswitches, e.g., provided on an exterior surface of the base 51. The user may activate and/or program the lighting effects by pressing down on the microswitch, which may be movable directly or indirectly via the closure 20, to toggle between an ON state and an OFF state.

To facilitate the above-described visual indications, system 12 may facilitate leakage of visible light to one or more particular locations, as represented in FIG. 4B. This leakage of light may provide the indication that oral disinfection system 12 is actively disinfecting an oral device 14 contained therein. For example, at least some leaked light may illuminate an outer periphery of lid 30 at the interface of lid 30 and body 22, so as to provide lid illumination 90. If desired, an interior surface of wall 32 and/or an inner surface of wall 72 may be formed with a light-reflecting coating or material in order to guide light and provide lid illumination 90. As shown in FIG. 4B, lid illumination 90 may tend to follow the shape or outline of rim 36 (shown in FIG. 1) and the inner periphery of body 22. Additionally, light 81, including visible light, may provide illumination to an entirety of body 22. This light may tend to illuminate the edge surfaces of body 22 so as to cause these surfaces to appear brighter. For example, an illuminated outer edge 88 of body 22 may appear brighter than adjacent portions of body 22, such as central regions of walls 24. The leakage of light may be sufficient to illuminate body 22 by an amount that allows body 22 to be readily identified by the human eye in a darkened environment, akin to a night-time light.

The leakage of light 81, including visible light, may be light generated from a single type of light source 82, e.g., a UVC light source configured to generate an amount of UVC light sufficient to disinfect oral device 14, as described above. In some aspects, in order to control an amount of UVC light that leaks to an outside of system 12, body 22 may be formed of a material that partially or entirely blocks UVC light. In such a case, light 81 that exits body 22 may be free or substantially free of UVC light. In some aspects, body 22 may be substantially transparent to UVC light, and an amount of UVC light that leaks outside of closure 20 is reduced to a safe intensity due to, for example, blockage of some of the UVC light by the geometry of closure 20 and wall 72.

Figure 5B:
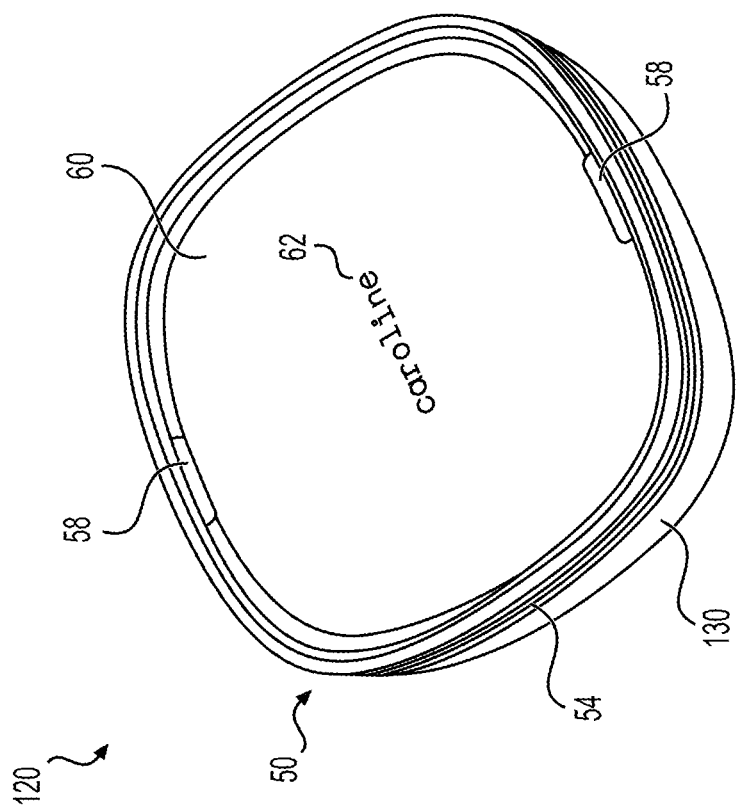
FIG. 5B is a perspective view of the bottom of the mobile storage system of FIG. 5B.
Figure 5A:
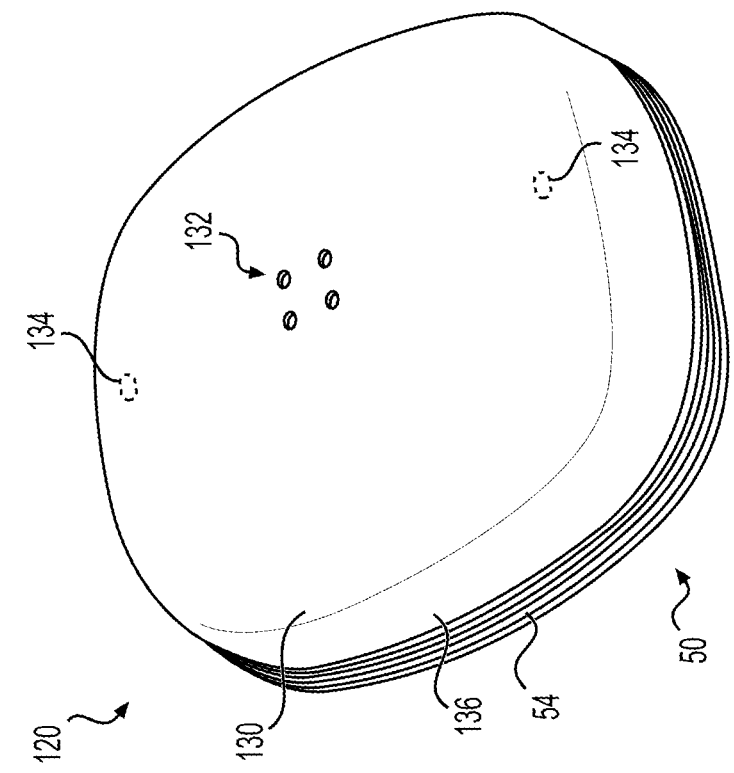
FIG. 5A is a perspective view of a mobile storage system according to an embodiment of the disclosure.

FIGS. 5A and 5B illustrate a mobile storage system 120 which may be included as part of oral disinfection system 12 or as a separate system. In some aspects, mobile storage system 120 may include case 50 having an outer textured surface 54, as described above with respect to FIGS. 1 and 2, for example. Case 50 may include a personalization 62, if desired, with suitable identification information. In order to increase the mobility of mobile storage system 120, a lid 130 may be provided in place of lid 30. Lid 130 may be formed without a prism or other light-directing body on an outer surface of a peripherally-extending wall 136. Wall 136 may have similar features as wall 32 of lid 30. Additionally, lid 130 may be formed with one or more of the features discussed above with respect to lid 30 (e.g., upper cavity 34, rim 36, and cap 38).

Lid 130 may include one or more features to provide ventilation via the top and/or bottom of mobile storage system 120. For example, lid 130 may include one or more centrally-disposed central vents 132 at a top surface of lid 130. While four central vents 132 are illustrated in FIG. 5A, one, two, three, five, or more central vents 132 may be formed in lid 130. If desired, one or more upward-facing vents 134 may be formed at a peripheral portion of lid 130. While two peripheral vents 134 are illustrated, one, three, or four peripheral vents 134 may be formed through lid 130. Additionally, each peripheral vent 134 may include a plurality of through-holes to increase ventilation, while preventing the entry of large contaminants. Case 50 may also include one or more ventilation mechanisms, such as vents 58, so as to provide air flow from both the top and bottom of mobile storage system 120. By virtue of the features that provide ventilation, the mobile storage system 120 allows for proper evaporation of liquid that may be present in the case 50.

Figure 6:
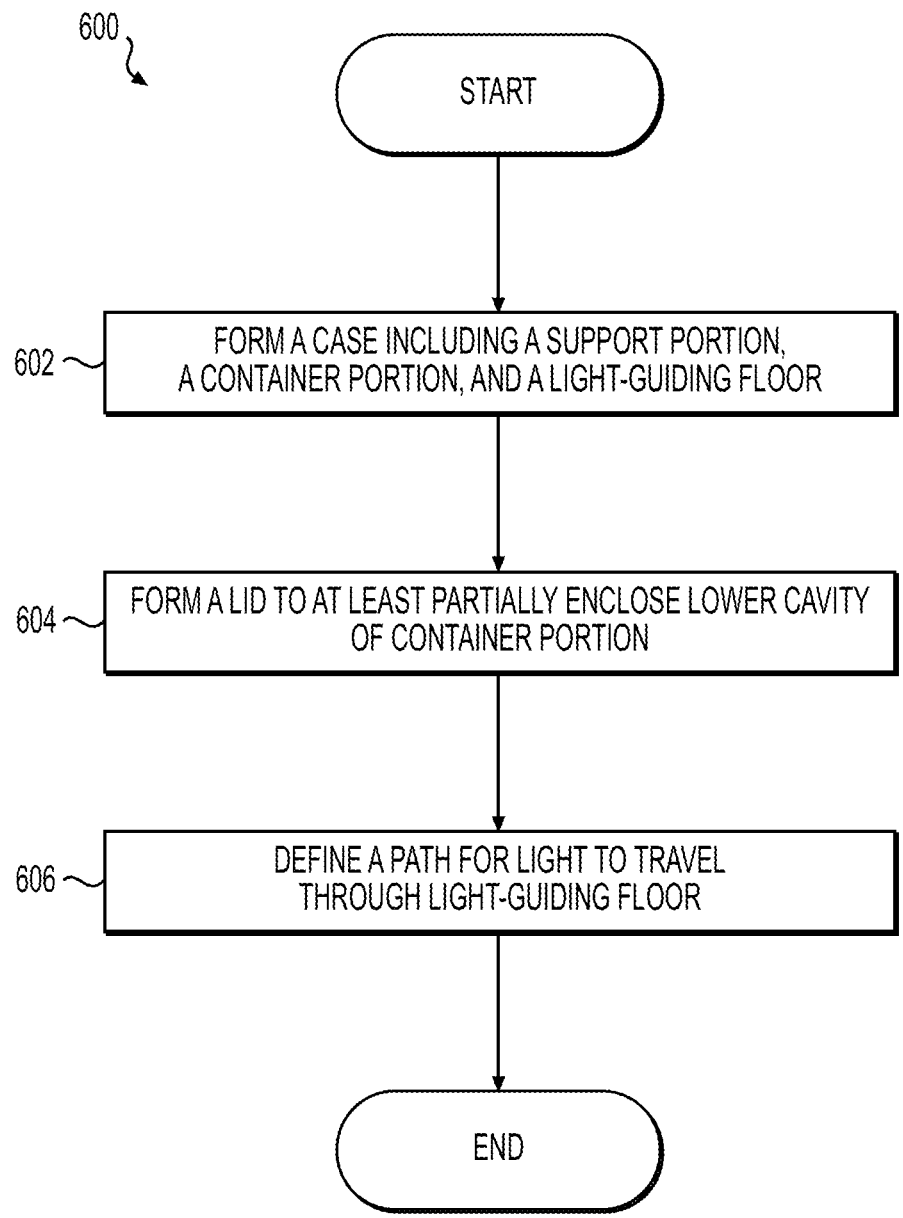
FIG. 6 is a flowchart illustrating an exemplary method according to an embodiment of the disclosure.

FIG. 6 is a flowchart showing an exemplary process 600 for disinfection or sanitation with oral disinfection system 12. In a step 602, a case, e.g., case 50, may be formed with any of the above-described features. For example, as described above, case 50 may be formed with a support portion 52, container portion 70, and light-guiding floor 76. In some aspects, step 602 may also include forming disinfecting base 51. For example, base 51 may be formed with a recess to removably receive case 50. Alternatively, case 50 may be integrally formed with disinfecting base 51.

Step 604 may include forming a lid, such as lid 30, that is configured to at least partially enclose the lower cavity 74 formed by container portion 70 of case 50. Lid 30 may be formed with any of the above-described features, and may be formed within a body 22 to facilitate transmission of visible light to an observer of oral disinfection system 12.

Step 606 may include defining a path for light to travel, for example, to a location outside of lid 30 and through a body 22. Step 606 may include defining a path for leakage of light between wall 32 and wall 72, for example, such that light may exit lid 30. Step 606 may also include providing disinfecting base 51 with a light source 82 for transmitting UVC light through light-guiding floor 76 As such, a path of light from source 82 through floor 76 may form a first path. A path for leakage of light to body 22 and outside of system 12 may form a second path formed in step 606.

By virtue of the oral disinfection system 12 of the present disclosure, disinfection of an oral device 14 may be performed while providing a visual indication of this disinfection. For example, a controlled amount of light may leak from a UVC light source to an exterior of a case 50 and cap 38 so as to provide light to an illuminable body such as a body 22. This light may be useful for locating the system 12 in a darkened environment, and may provide a user with increased confidence regarding the efficacy of sanitation. The case 50 and cap 38 of the present disclosure also provide decorative tabletop storage for a mouthguard, retainer, clear aligners, or other dental, medical, or personal devices associated with use in the mouth. In addition, the case 50 and cap 38 of the present disclosure provide storage for a mouthguard, retail, clear aligners, or other dental, medical, or personal devices that can easily be stored and carried for travel.

It will be apparent to those skilled in the art that various modifications and variations can be made to the disclosed oral device without departing from the scope of the disclosure. Other embodiments of the oral device will be apparent to those skilled in the art from consideration of the specification and the accompanying figures. It is intended that the specification, and, in particular, the examples provided herein be considered as exemplary only, with a true scope of the disclosure being indicated by the following claims and their equivalents.

We claim:

1. An oral device storage system comprising:
   a case configured to receive an oral device, the case including a support portion defining a lower portion of the case, an outer textured surface, a personalization, and a peripherally extending first wall surface;
   a lid configured to be placed on and cover the case, the lid including a peripherally extending second wall surface and one or more vents;
   a lower cavity defined by the peripherally extending first wall surface of the case; and
   an upper cavity defined by the peripherally extending second wall surface of the lid.

2. The oral device storage system of claim 1, wherein the outer textured surface has a plurality of grooves and recesses.

3. The oral device storage system of claim 1, wherein a shape of the peripherally extending second wall surface of the lid and the upper cavity is one of a circle, an ovoid, a rectangle, or a square.

4. The oral device storage system of claim 1, wherein the one or more vents are disposed in a central region of a top surface of the lid.

5. The oral device storage system of claim 1, wherein the one or more vents are formed at a peripheral portion of the lid.

6. The oral device storage system of claim 5, wherein each of the one or more vents include a plurality of through-holes.

7. The oral device storage system of claim 1, wherein the peripherally extending second wall surface includes a rim defining a bottom lip of the peripherally extending second wall surface, wherein in a closed configuration, the rim abuts the outer textured surface.

8. An oral device storage system comprising:
   a case configured to receive an oral device, the case including:
      a support portion defining a lower portion of the case, and including a peripherally extending first wall surface; and
      a lid configured to be placed on and cover the case, the lid including a second peripherally extending wall surface and one or more features to provide ventilation, wherein, in a closed configuration, the peripherally extending second wall surface surrounds the peripherally extending first wall surface, and the lid is positioned relative to the support portion such that the case is configured to retain an oral device positioned therein.

9. The oral device storage system of claim 8, wherein the support portion includes one or more features to provide ventilation.

10. The oral device storage system of claim 8, wherein the case includes a personalization feature.

11. The oral device storage system of claim 8, wherein the one or more features to provide ventilation includes one or more vents disposed in a central region of a top surface of the lid.

12. The oral device storage system of claim 8, wherein the one or more features to provide ventilation includes one or more vents formed at a peripheral portion of the lid.

13. The oral device storage system of claim 12, wherein each of the one or more vents formed at the peripheral portion of the lid includes a plurality of through-holes.

14. The oral device storage system of claim 8, wherein the one or more features to provide ventilation includes one or more vents disposed in a central region of a top surface of the lid and one or more vents formed at a peripheral portion of the lid.

15. An oral device storage system comprising:
   a case configured to receive an oral device, the case including a support portion defining a lower portion of the case, and including a peripherally-extending wall surface;
   a first lid configured to be placed on and cover the case in a first assembled state, the first lid including a peripherally extending wall configured to mate with the case in the first assembled state;
   a second lid configured to be placed on and cover the case in a second assembled state, the second lid including an illuminable body; and
   one or more features to provide ventilation.

16. The oral device storage system of claim 15, wherein the case includes an outer textured surface.

17. The oral device storage system of claim 15, wherein the one or more features to provide ventilation include one or more vents disposed in a central region of a top surface of the lid.

18. The oral device storage system of claim 15, wherein the one or more features to provide ventilation include one or more vents formed at a peripheral portion of the lid.

19. The oral device storage system of claim 18, wherein each of the one or more vents formed at a peripheral portion of the lid includes a plurality of through-holes.

* * * * *